(12) United States Patent
Oikawa et al.

(10) Patent No.: US 12,724,907 B2
(45) Date of Patent: Sep. 1, 2026

(54) INFORMATION TRANSMISSION SYSTEM, INFORMATION OUTPUT DEVICE, AND INFORMATION TRANSMISSION METHOD

(71) Applicant: Hitachi High-Tech Corporation, Tokyo (JP)

(72) Inventors: Michio Oikawa, Tokyo (JP); Yoshiharu Iwata, Tokyo (JP); Hikari Nishimura, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 205 days.

(21) Appl. No.: 18/687,129

(22) PCT Filed: Feb. 6, 2023

(86) PCT No.: PCT/JP2023/003839
§ 371 (c)(1),
(2) Date: Feb. 27, 2024

(87) PCT Pub. No.: WO2023/171196
PCT Pub. Date: Sep. 14, 2023

(65) Prior Publication Data
US 2025/0013765 A1 Jan. 9, 2025

(30) Foreign Application Priority Data
Mar. 10, 2022 (JP) ................................ 2022-037605

(51) Int. Cl.
*G06F 21/62* (2013.01)
*G06K 19/06* (2006.01)
*G16H 10/60* (2018.01)

(52) U.S. Cl.
CPC ....... *G06F 21/62* (2013.01); *G06K 19/06037* (2013.01); *G16H 10/60* (2018.01)

(58) Field of Classification Search
CPC ... G06F 21/62; G06K 19/06037; G16H 10/60
See application file for complete search history.

(56) References Cited

U.S. PATENT DOCUMENTS 6,581,075 B1 * 6/2003 Guturu .................. G06F 16/273
9,107,065 B2 * 8/2015 Dharawat ............ H04W 12/02
(Continued)

FOREIGN PATENT DOCUMENTS

CN 102034127 A 4/2011
JP 2002-55866 A 2/2002
JP 2019-079503 A 5/2019

OTHER PUBLICATIONS

International Search Report of PCT/JP2023/003839 dated Apr. 25, 2023.
(Continued)

*Primary Examiner* — Nam T Tran
(74) *Attorney, Agent, or Firm* — MATTINGLY & MALUR, PC

(57) ABSTRACT

It is possible to exchange highly confidential information between information systems of which networks are separated from each other. An information transmission system includes: an information output device that stores information to be shared, generates concealed data by compressing and concealing the information to be shared using a predetermined concealment method, and generates a two-dimensional barcode loaded with the concealed data but not loaded with concealment information indicating the concealment method; and an information input system that stores the concealment method in advance, decodes the two-dimensional barcode to acquire the concealed data, and decrypts the concealed data based on the concealment method.

7 Claims, 21 Drawing Sheets

(56) References Cited

U.S. PATENT DOCUMENTS

| | | | | |
|---|---|---|---|---|
| 12,266,430 | B2 * | 4/2025 | Gergely | G16H 10/60 |
| 2013/0112760 | A1 * | 5/2013 | Schory | G06K 19/06037 235/494 |
| 2014/0070012 | A1 * | 3/2014 | Hunt | G06K 19/06037 235/494 |
| 2015/0358164 | A1 * | 12/2015 | Carter | G06K 19/06037 713/179 |
| 2017/0243041 | A1 * | 8/2017 | Arce | G06K 19/06037 |
| 2019/0244198 | A1 * | 8/2019 | Waters | G06K 19/06037 |
| 2019/0306094 | A1 * | 10/2019 | Liu | H04L 67/53 |
| 2019/0356479 | A1 * | 11/2019 | Grimme | G16H 10/60 |
| 2020/0380493 | A1 * | 12/2020 | Morales | G06K 19/06037 |
| 2021/0303809 | A1 * | 9/2021 | Roux | G06K 19/06037 |
| 2022/0208315 | A1 * | 6/2022 | Strohl | G16H 10/60 |

OTHER PUBLICATIONS

Japanese Office Action received in corresponding Japanese Application No. 2022-037605 dated Oct. 14, 2025.

* cited by examiner

[FIG. 1]
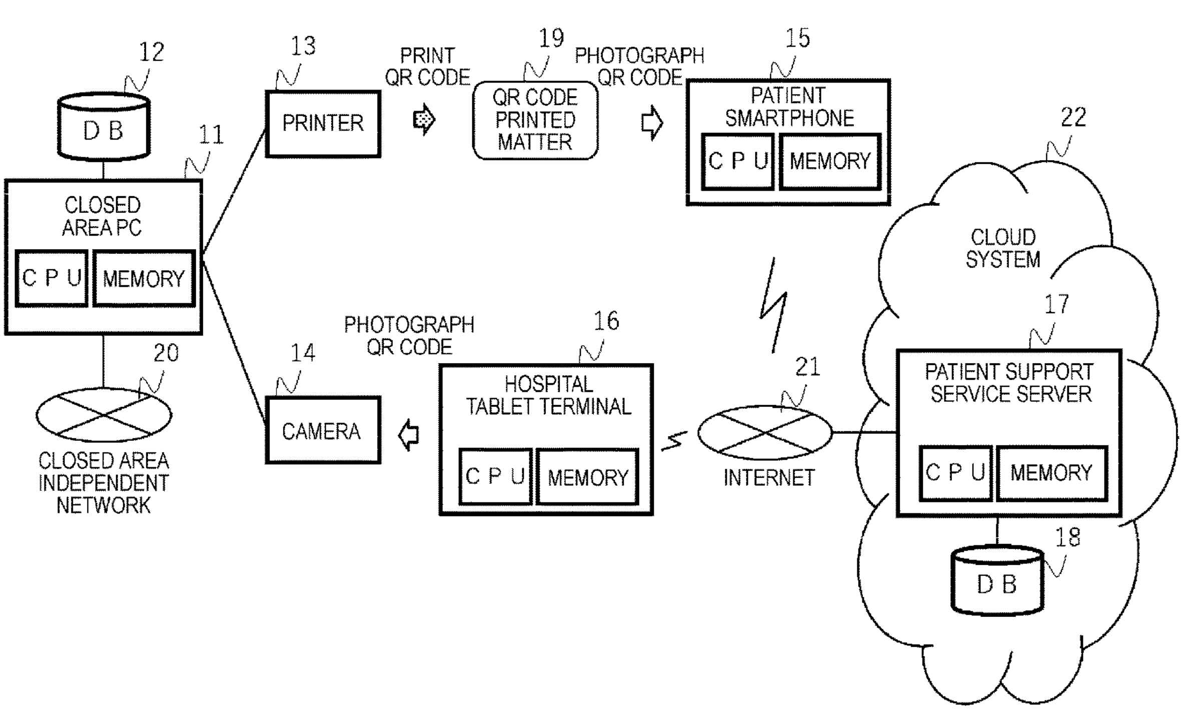

□□□□ PATIENT (P10354) 31

OO HOSPITAL (H0123) 32

HOSPITAL IDENTIFICATION INFORMATION
& INDIVIDUAL TREATMENT INFORMATION QR CODE

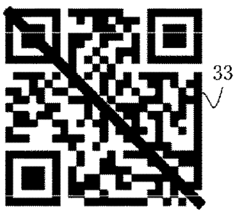

33

FUTURE SCHEDULE 34

| SUN | MON | TUE | WED | THU | FRI | SAT |
|---|---|---|---|---|---|---|
| | 1 | 2 MEDICAL EXAMINATION 10:00 | 3 TREATMENT 11:20 | 4 TREATMENT 10:40 | 5 TREATMENT 13:30 | 6 |
| 7 | 8 TREATMENT 10:30 | 9 TREATMENT 10:30 | 10 MEDICAL EXAMINATION 9:00 TREATMENT 10:00 | 11 TREATMENT 14:00 | 12 TREATMENT 14:30 | 13 |
| 14 | 15 TREATMENT 13:30 | 16 TREATMENT 14:30 | 17 MEDICAL EXAMINATION 14:00 TREATMENT 14:30 | 18 TREATMENT 10:30 | 19 TREATMENT 10:30 | 20 |
| 21 | 22 TREATMENT 11:30 | 23 TREATMENT 11:30 | 24 | 25 | 26 | 27 |
| 28 | 29 | 30 MEDICAL EXAMINATION 10:00 | | | | |

[FIG. 3]
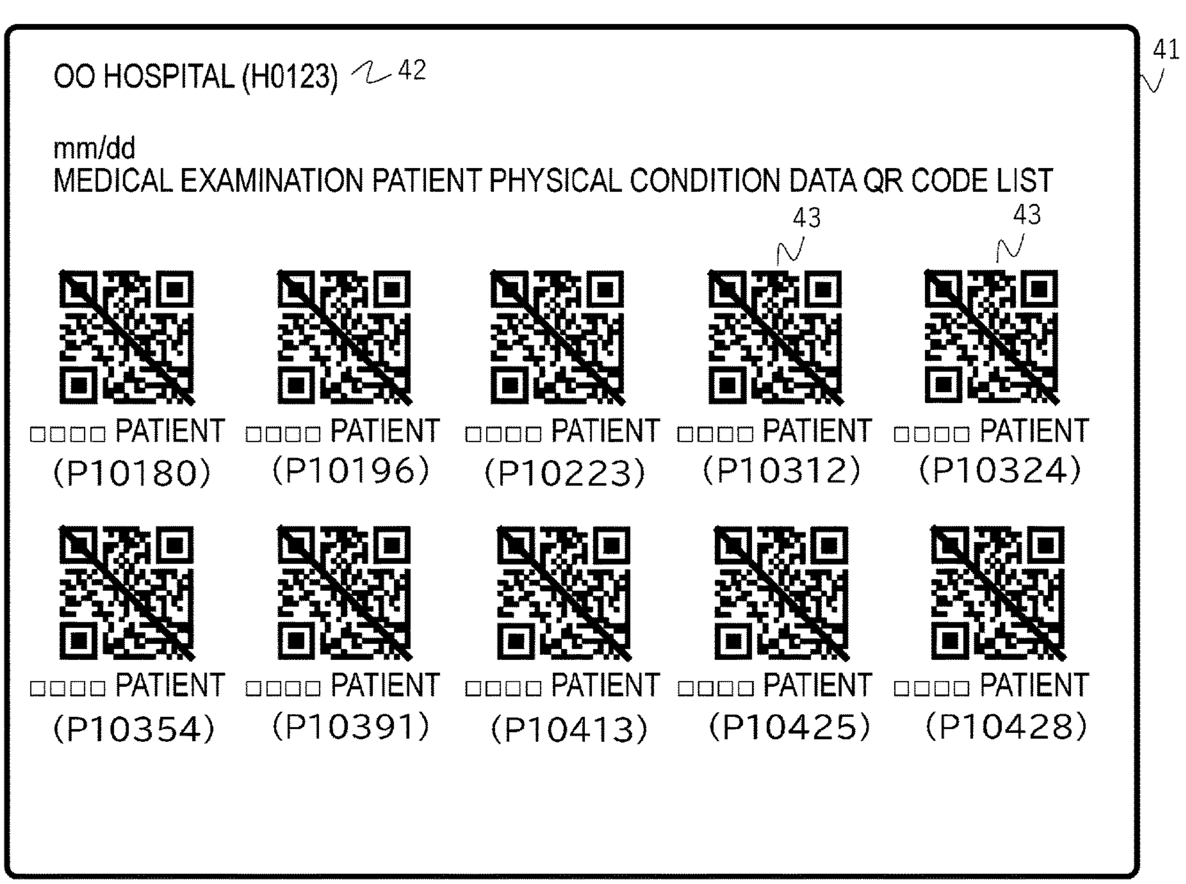

[FIG. 4]
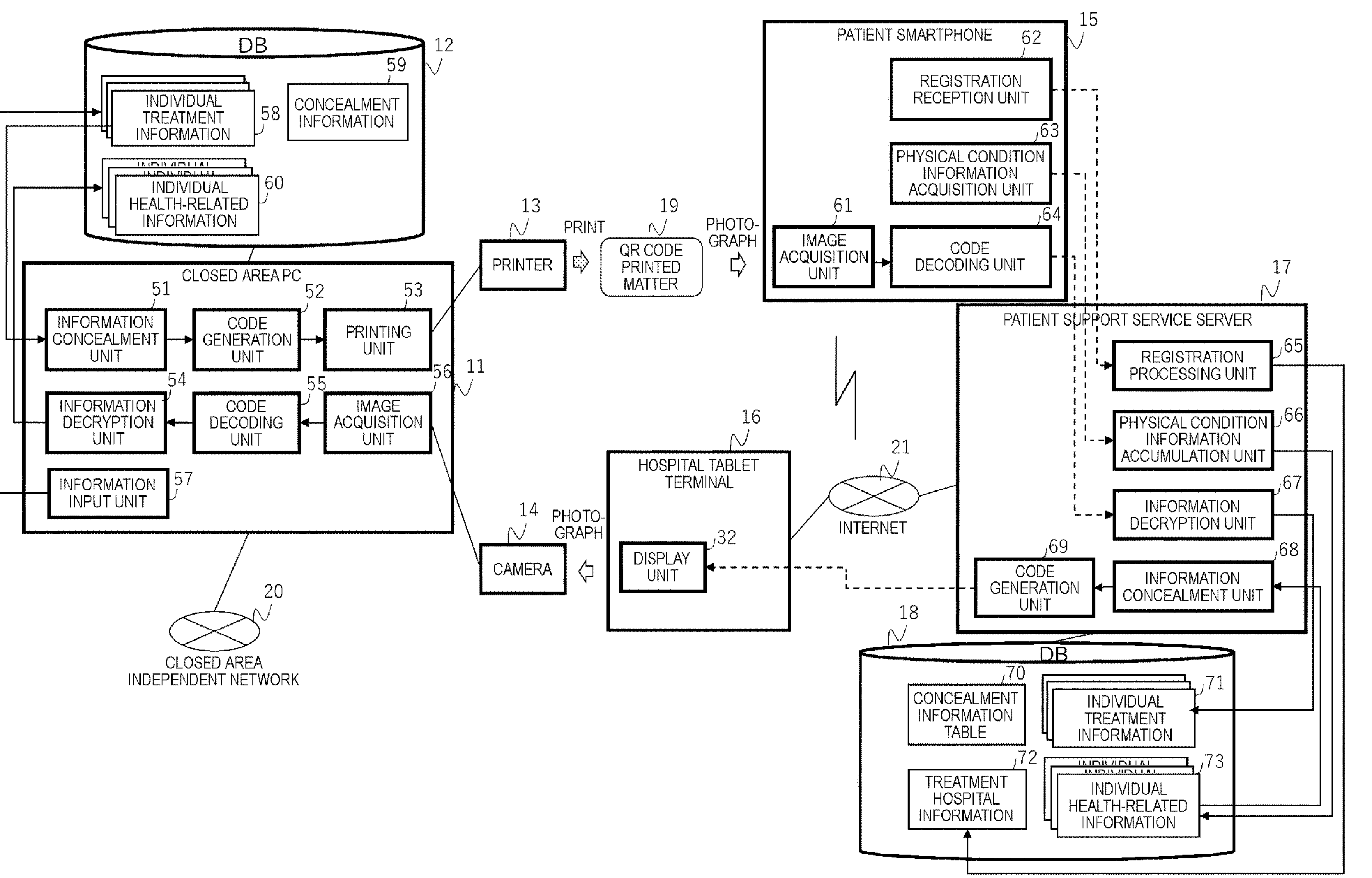

[FIG. 5]
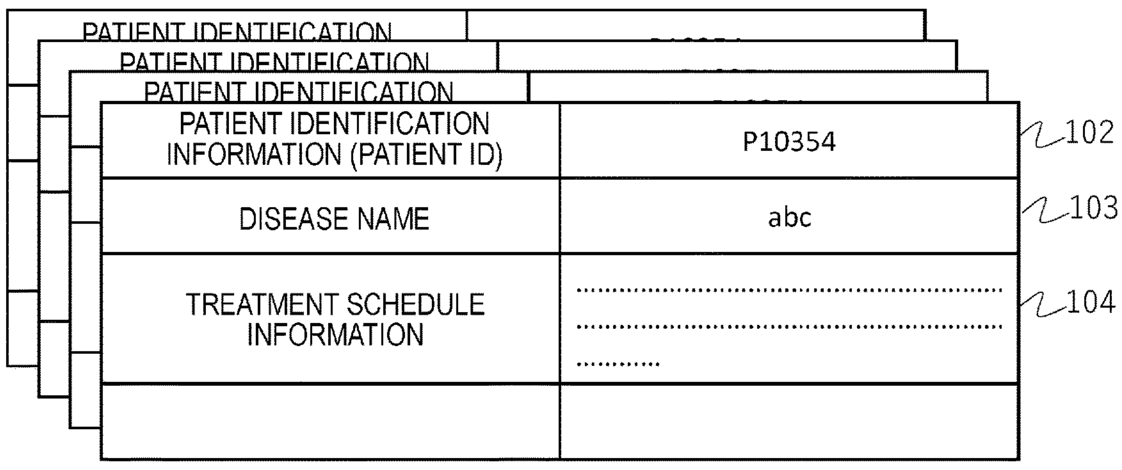
INDIVIDUAL TREATMENT INFORMATION

[FIG. 6]

| PATIENT IDENTIFICATION INFORMATION (PATIENT ID) | P10354 |
| --- | --- |
| DATE | yyyy/mm/dd |
| HEALTH STATUS | GOOD |
| BODY TEMPERATURE | nn.n DEGREES |
| BLOOD PRESSURE | kkk |
| ⋮ | ⋮ |

121
122
123
124
125

60,73

INDIVIDUAL HEALTH-RELATED INFORMATION

[FIG. 7]

| HOSPITAL IDENTIFICATION INFORMATION (HOSPITAL ID) | CONCEALMENT INFORMATION (COMPRESSION METHOD) |
|---|---|
| H0122 | xxxx |
| H0123 | yyyy |
| H0124 | zzzz |
| | |

92 93

CONCEALMENT INFORMATION TABLE 70

| PATIENT IDENTIFICATION INFORMATION (PATIENT ID) | HOSPITAL IDENTIFICATION INFORMATION (HOSPITAL ID) |
|---|---|
| P10354 | H0123 |
| P10355 | H0987 |
| P10356 | H0456 |
| . . . | . . . |

TREATMENT HOSPITAL INFORMATION

72

[FIG. 9]
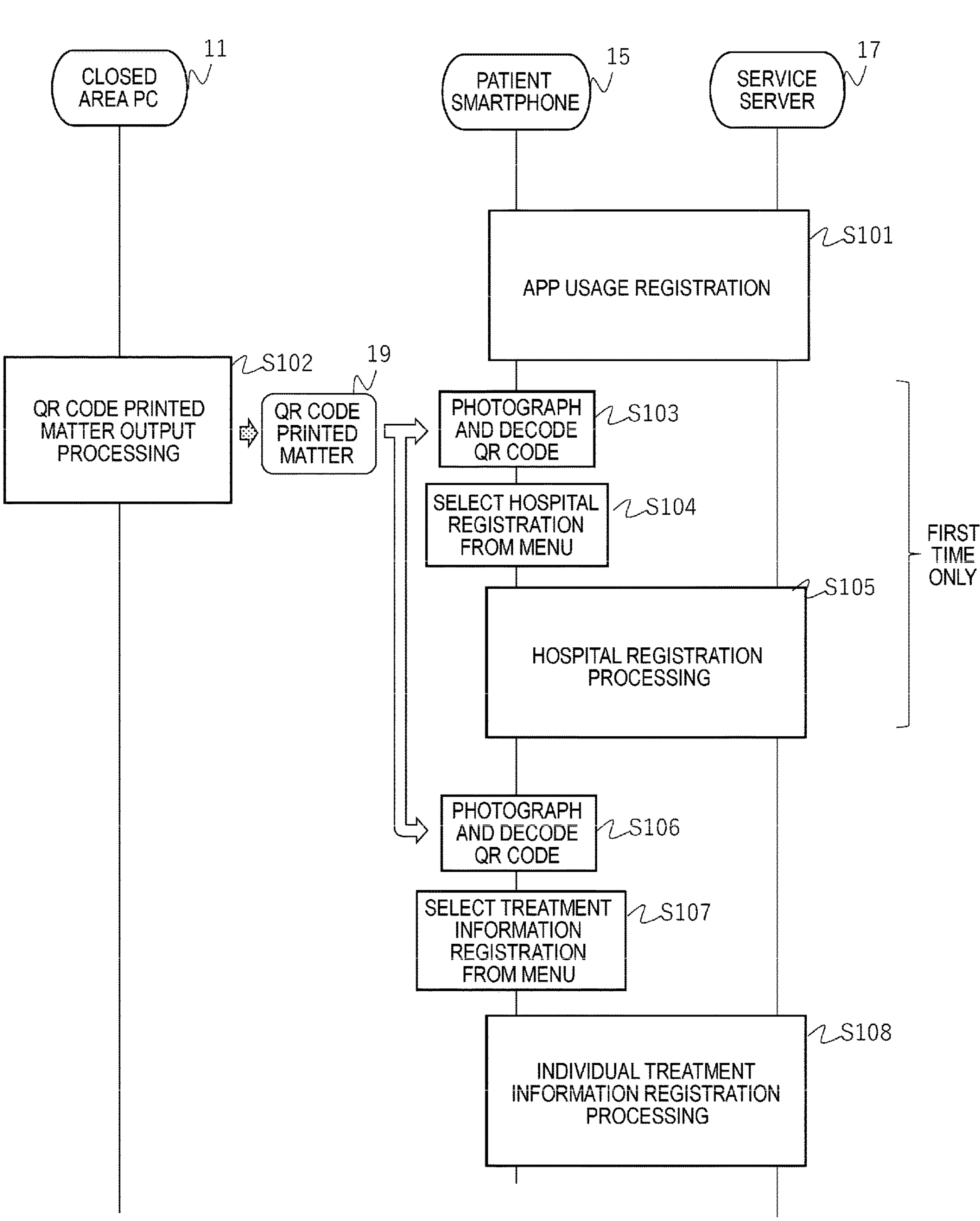

[FIG. 10]
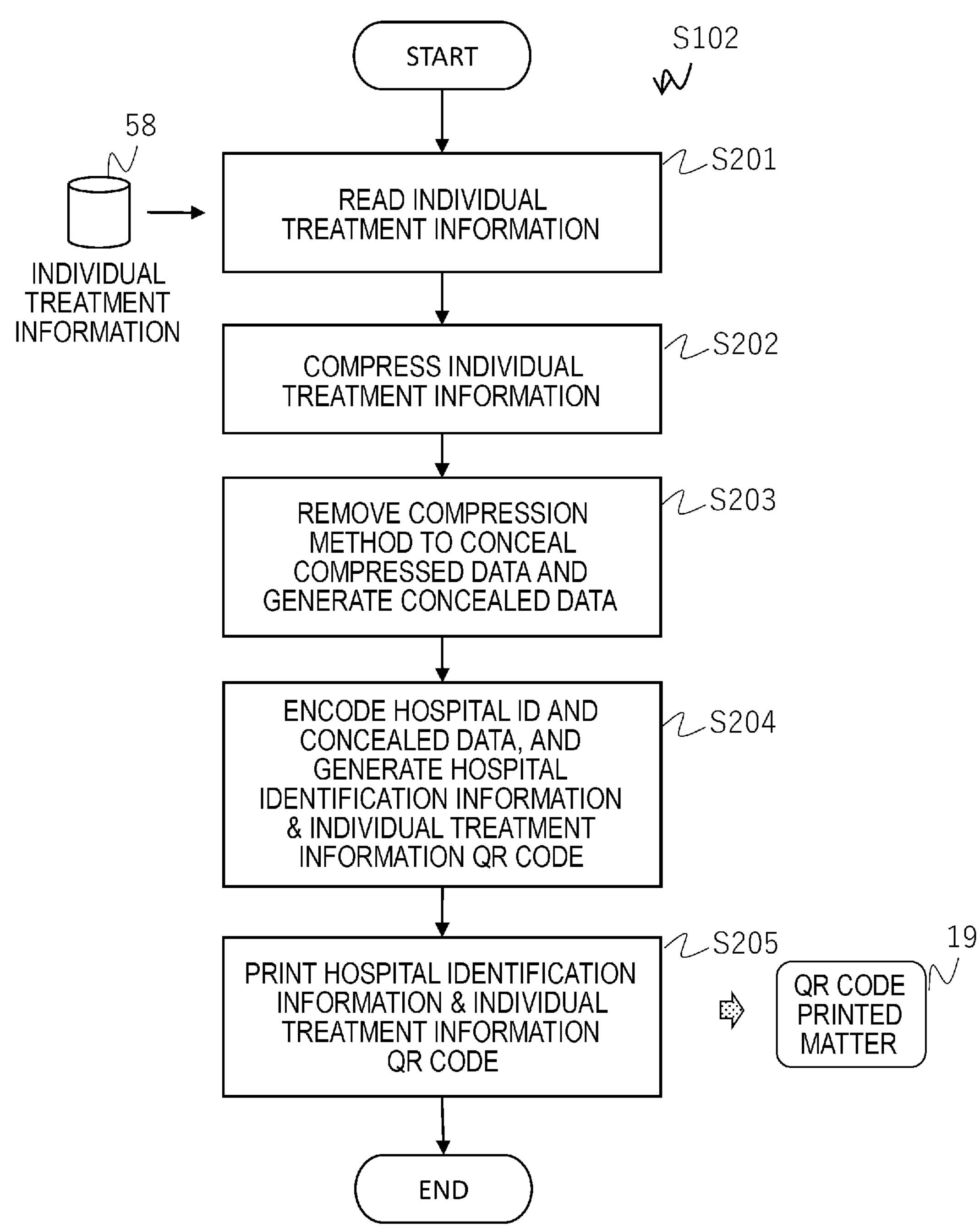

[FIG. 11]
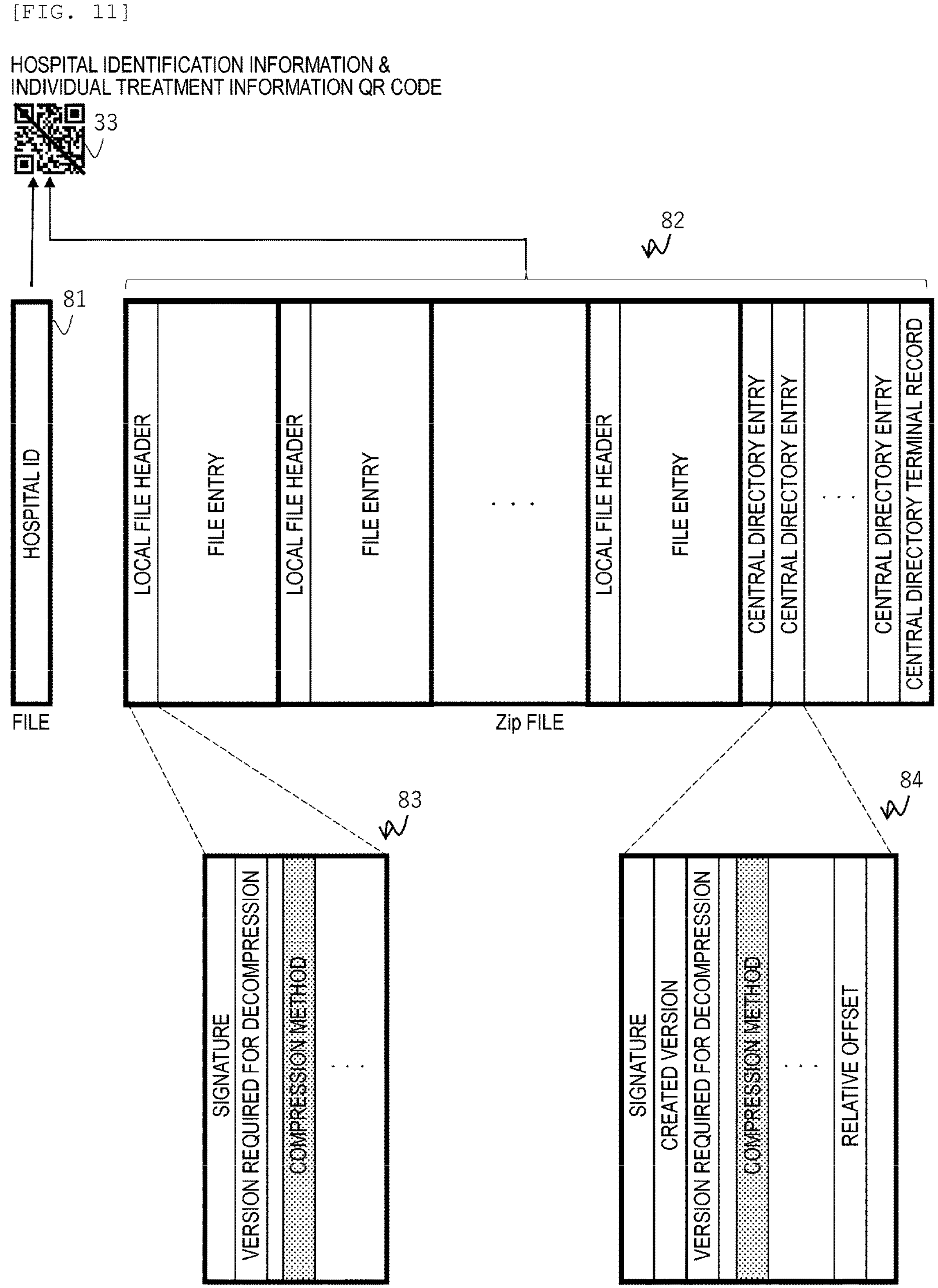

[FIG. 12]
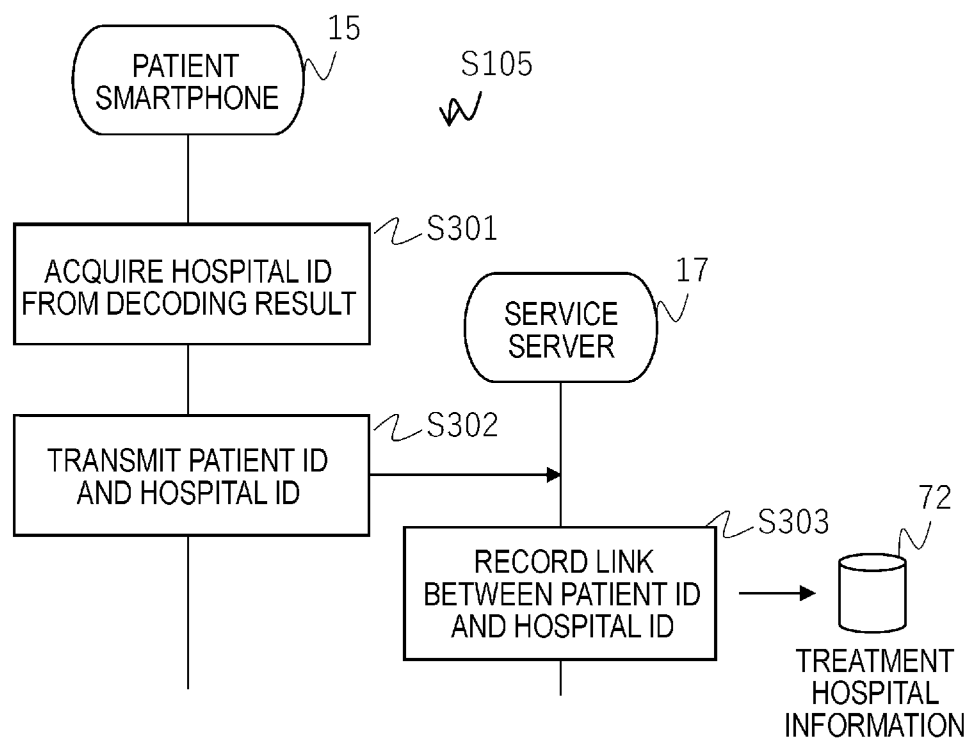

[FIG. 13]
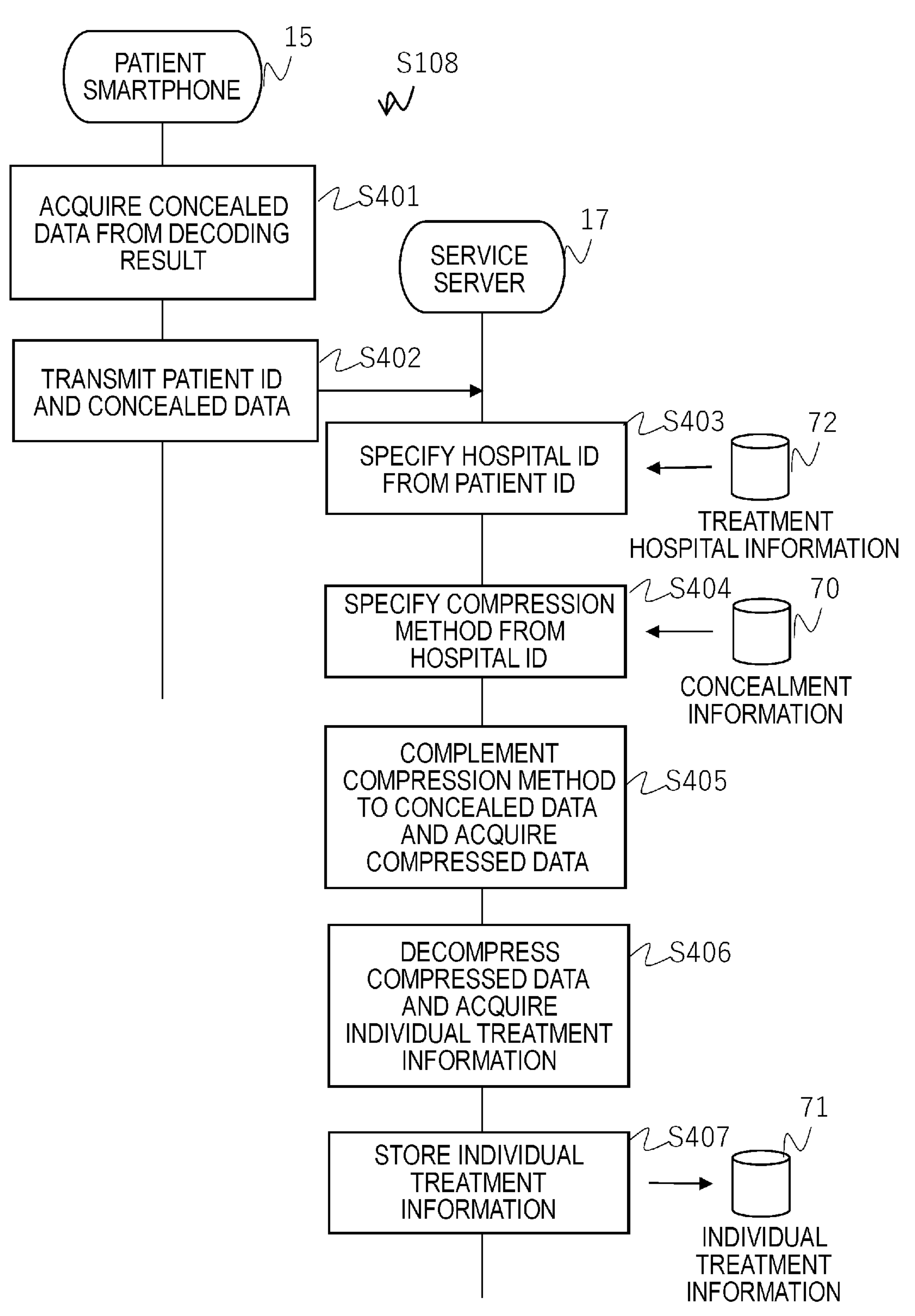

[FIG. 14]
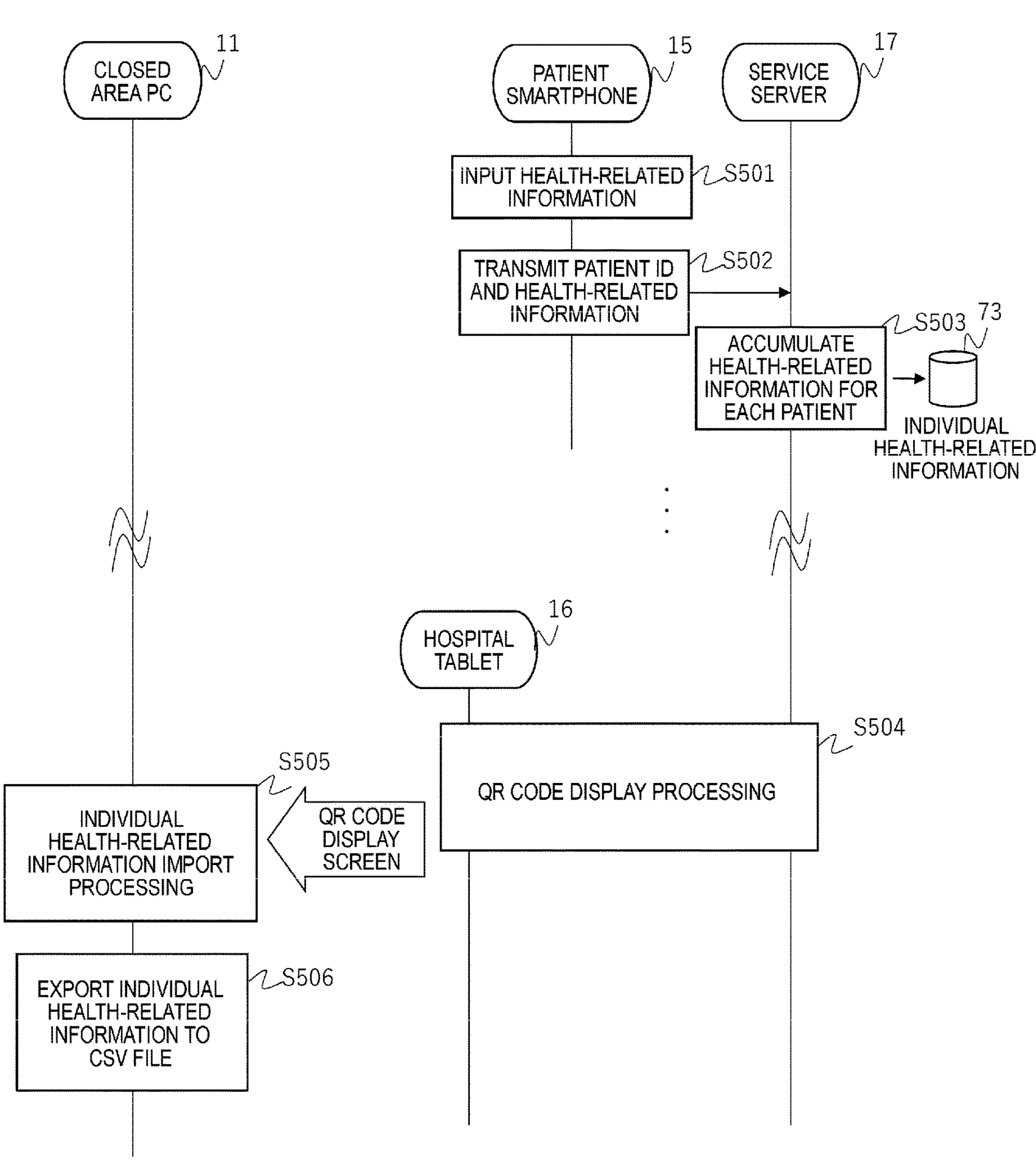

[FIG. 15]
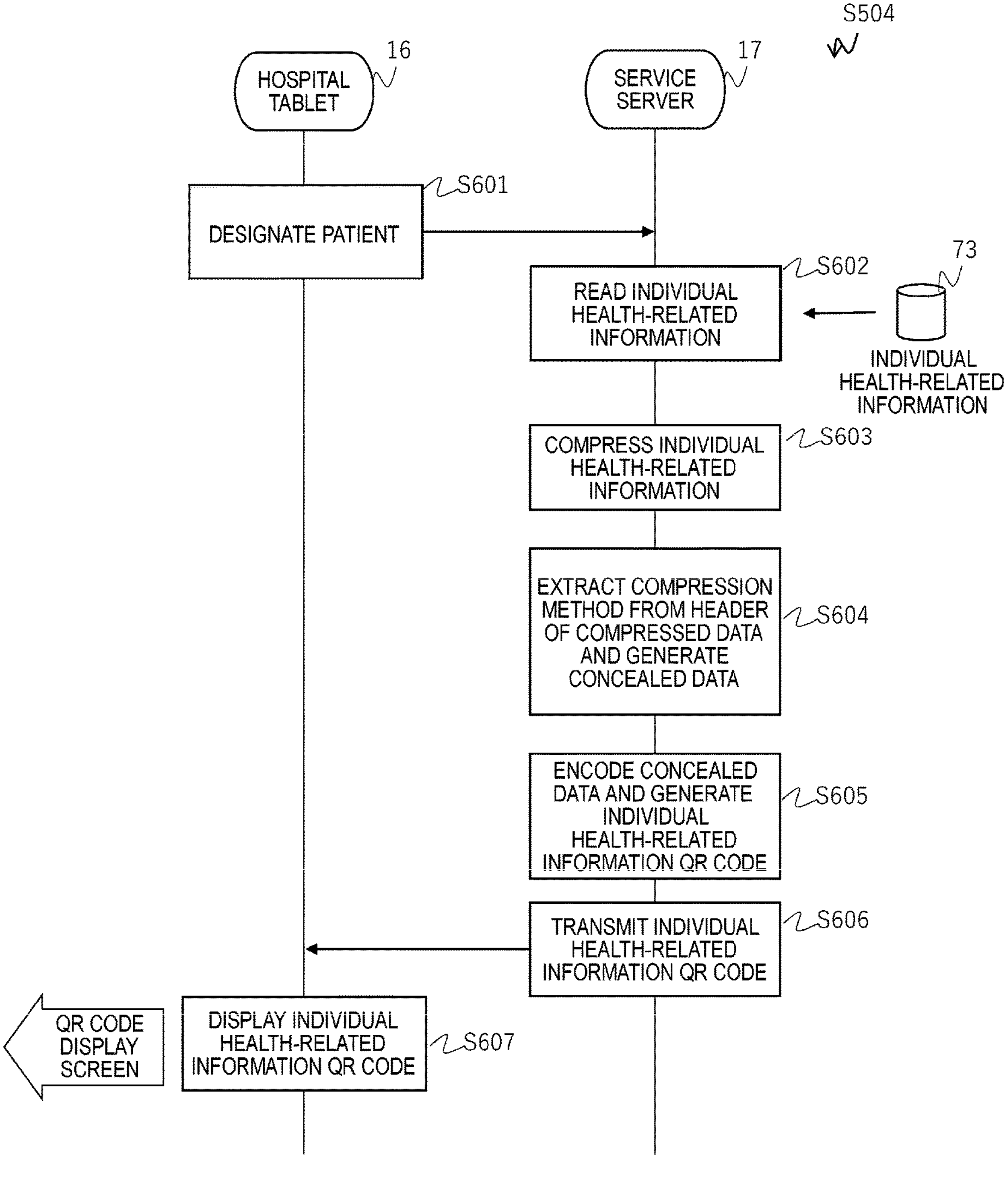

[FIG. 16]
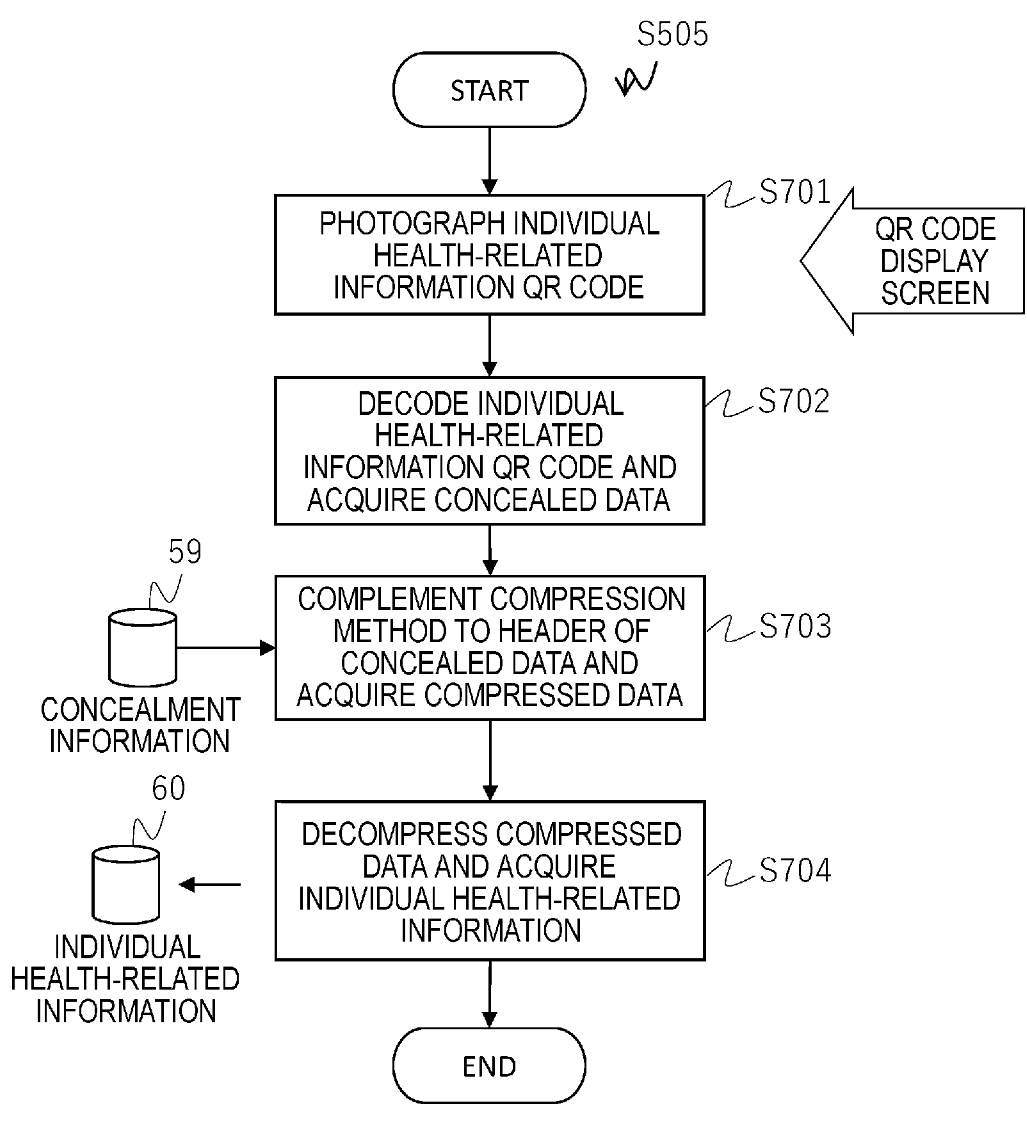

[FIG. 17]
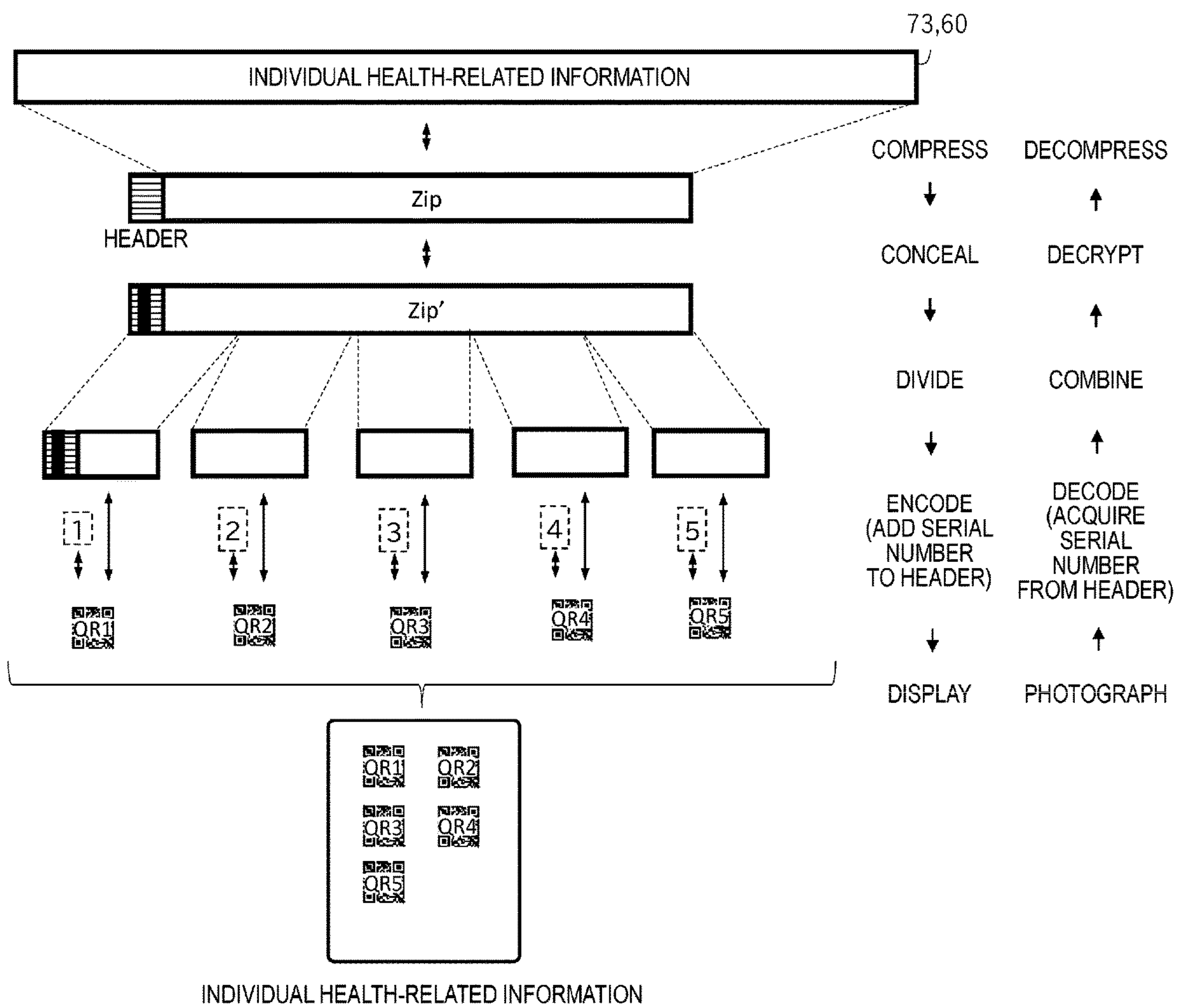

[FIG. 18]
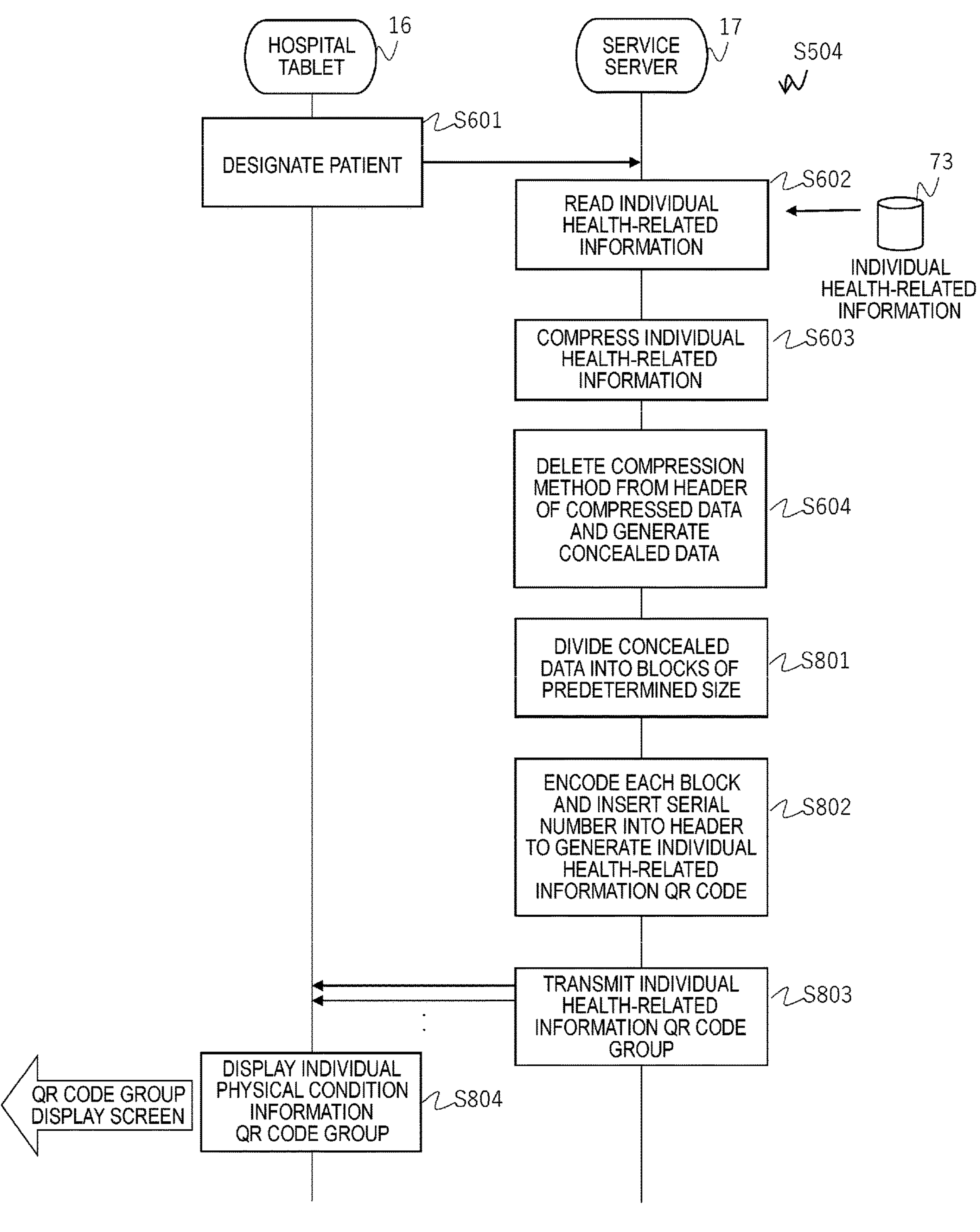

[FIG. 19]
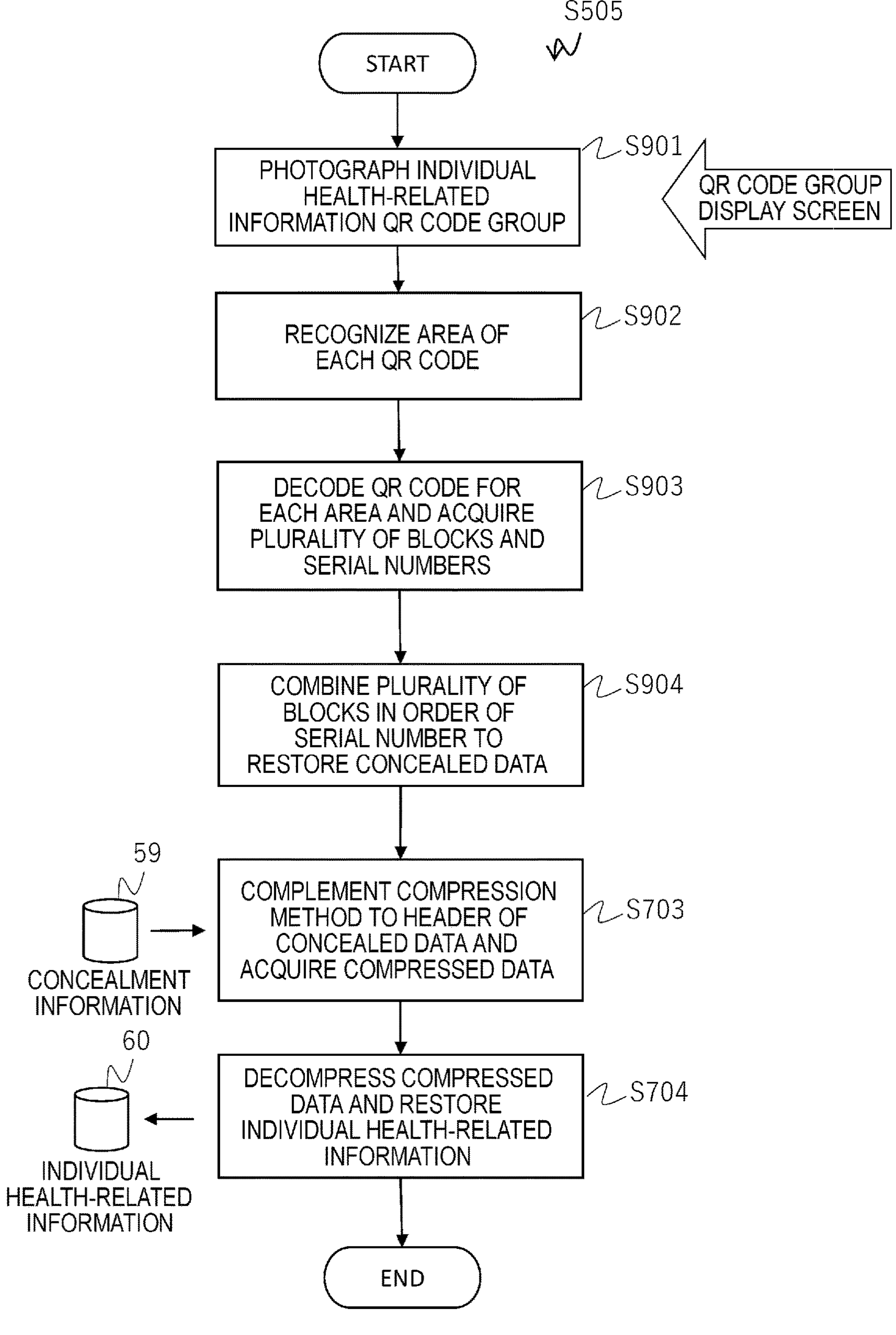

[FIG. 20]
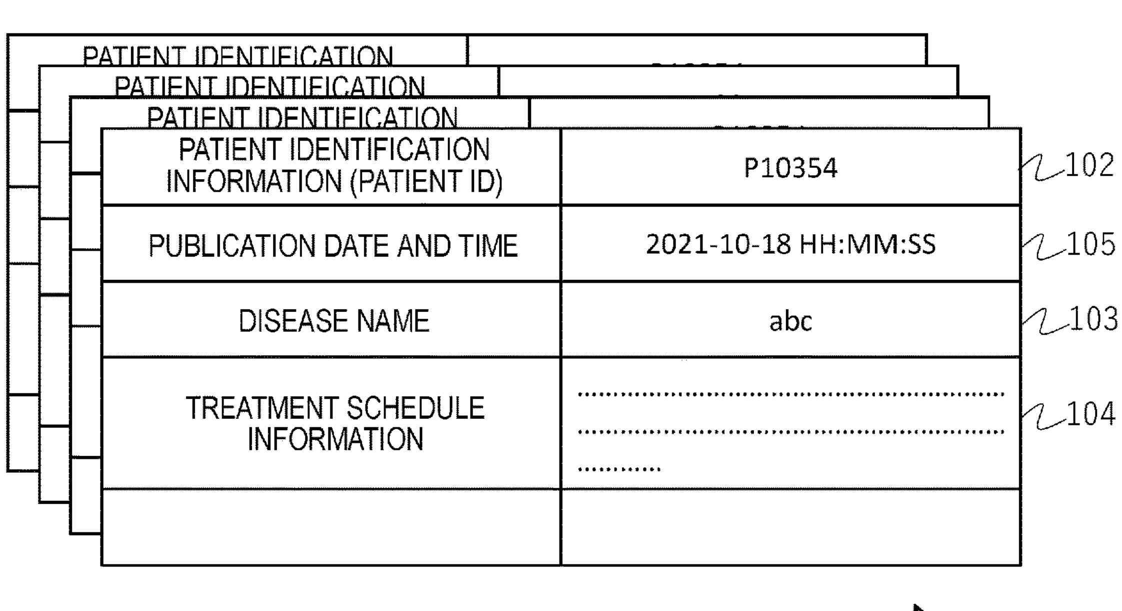

[FIG. 21]
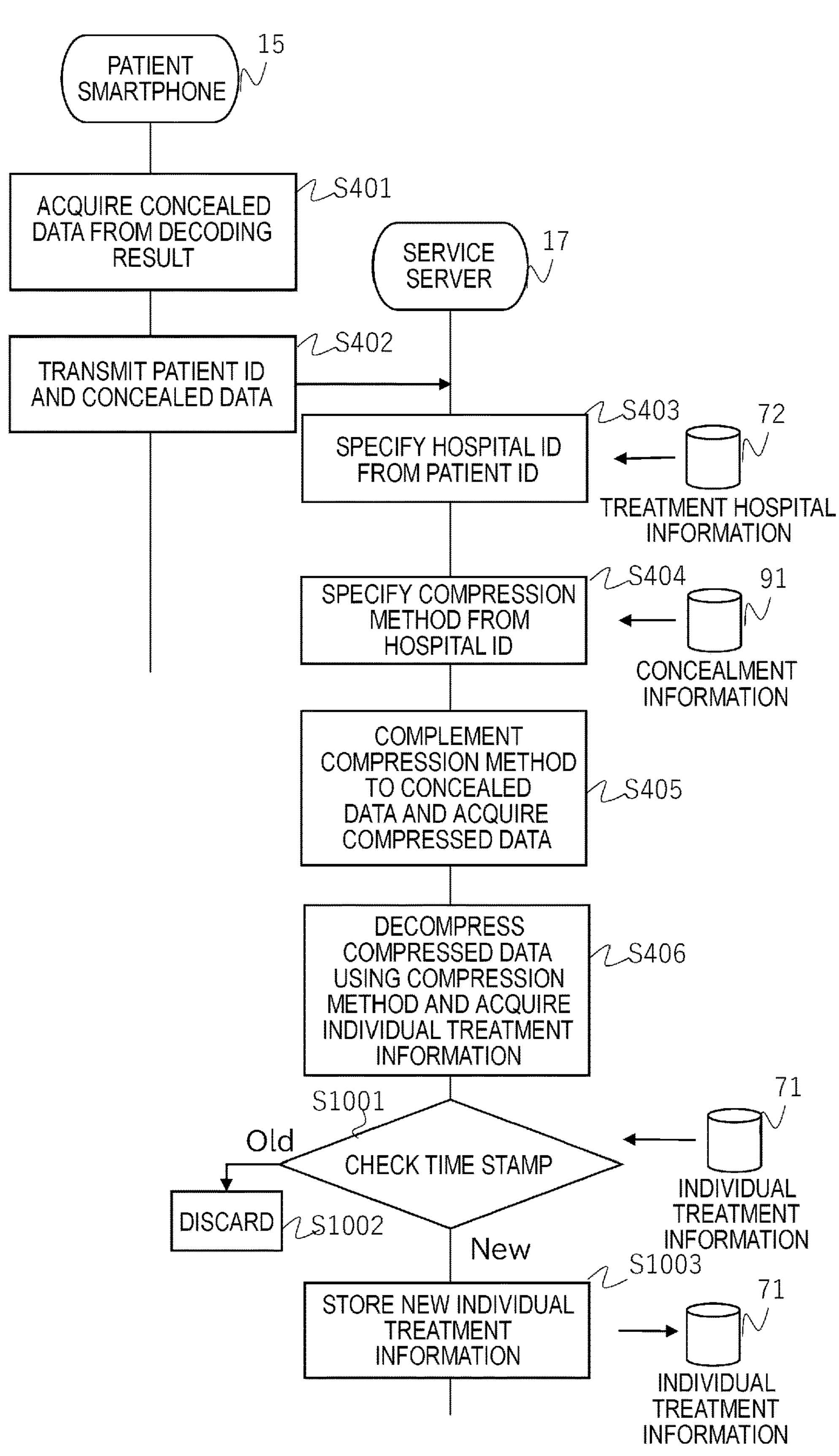

INFORMATION TRANSMISSION SYSTEM, INFORMATION OUTPUT DEVICE, AND INFORMATION TRANSMISSION METHOD

TECHNICAL FIELD

The present disclosure relates to a technology for transmitting information.

BACKGROUND ART

PTL 1 discloses a technology for importing interview contents obtained by a doctor's interview with a patient into an electronic medical record. Data on the interview contents are recorded on an interview server. On the other hand, electronic medical records are managed by an electronic medical record terminal device. A network to which the electronic medical record terminal device is connected is separated from the network to which the interview server is connected, that is, the Internet, and there is no terminal device that can be connected to both networks. This ensures high confidentiality of electronic medical records. When importing the interview contents recorded in the interview server into the electronic medical record, the interview server is accessed through a patient's personal terminal used by the patient or a terminal on the clinic side, and a two-dimensional barcode of the interview contents is displayed. Then, when a barcode reader is connected to the electronic medical record terminal device and the two-dimensional barcode is read, the data on the interview contents is imported into the electronic medical record of the electronic medical record terminal device.

CITATION LIST

Patent Literature

PTL 1: JP2019-79503A

SUMMARY OF INVENTION

Technical Problem

When a service system that supports patient health management and an information system of a hospital that treats patients can mutually use information, it will be beneficial for both health management and treatment. For example, by using the technology disclosed in PTL 1, it is possible to separate a hospital network that manages data such as electronic medical records from other networks such as the Internet, while enabling the exchange of information with the outside. However, in addition to separating a hospital network from other networks, security needs to be considered in various aspects. For example, a personal terminal of a patient such as a smartphone or a clinic-side terminal may be used at patient's home or in a public place. Then, there is a concern that the information stored in the two-dimensional barcode will be leaked by secretly photographing the screen. When the two-dimensional barcode is printed on a piece of paper for patient convenience, there is a concern that the information stored in the two-dimensional barcode will be leaked when the piece of paper is lost.

One object included in the present disclosure is to provide a technology that enables highly confidential information to be exchanged between information systems of which networks are separated from each other.

Solution to Problem

According to one aspect included in the present disclosure, there is provided an information transmission system including: an information output device that stores information to be shared, generates concealed data by compressing and concealing the information to be shared using a predetermined concealment method, and generates a two-dimensional barcode loaded with the concealed data but not loaded with concealment information indicating the concealment method; and an information input system that stores the concealment method in advance, decodes the two-dimensional barcode to acquire the concealed data, and decrypts the concealed data based on the concealment method.

Advantageous Effects of Invention

According to one aspect included in the present disclosure, since information is exchanged using a two-dimensional barcode that does not include concealment information, highly confidential information can be exchanged between devices of which networks are separated from each other.

BRIEF DESCRIPTION OF DRAWINGS

FIG. 1 is a schematic block diagram of a collaborative medical system according to Example 1.

FIG. 2 is a view showing an example of a QR code printed matter.

FIG. 3 is a view showing an example of a QR code display screen.

FIG. 4 is a block diagram showing a configuration of a collaborative medical system and each device.

FIG. 5 is a view showing an example of individual treatment information.

FIG. 6 is a view showing an example of individual health-related information.

FIG. 7 is a view showing an example of a concealment information table.

FIG. 8 is a view showing an example of treatment hospital information.

FIG. 9 is a flowchart of individual treatment information sharing processing.

FIG. 10 is a flowchart of QR code printed matter output processing.

FIG. 11 is a view showing an example of hospital identification information & individual treatment information QR code.

FIG. 12 is a flowchart of hospital registration processing.

FIG. 13 is a flowchart of individual treatment information registration processing.

FIG. 14 is a flowchart of individual physical condition-related information sharing processing.

FIG. 15 is a flowchart of QR code display processing.

FIG. 16 is a flowchart of individual health-related information import processing.

FIG. 17 is a conceptual diagram for describing processing regarding individual health-related information according to Example 2.

FIG. 18 is a flowchart of QR code display processing according to Example 2.

FIG. 19 is a flowchart of individual health-related information import processing according to Example 2.

FIG. 20 is a view showing an example of individual treatment information according to Example 3.

FIG. 21 is a flowchart of individual treatment information registration processing according to Example 3.

DESCRIPTION OF EMBODIMENTS

Hereinafter, embodiments of a collaborative medical system will be described.

Example 1

FIG. 1 is a schematic block diagram of a collaborative medical system according to Example 1. In the collaborative medical system, a hospital system connected to a closed area independent network 20 separated from the Internet 21, and a patient support service system connected to the Internet 21 share information.

A hospital information system is an information system that manages individual treatment information, which is information that requires confidentiality, such as individual medical record data of each patient in a hospital. The hospital information system includes a closed area personal computer (hereinafter also referred to as "PC") 11, a database 12, a printer 13, and a camera 14. The patient support service system is an information system for providing support regarding patient health management. The patient support service system includes a patient support service server 17, a patient smartphone (hereinafter also referred to as "smartphone") 15, and a database 18. The collaborative medical system includes a hospital tablet terminal 16 used by doctors and the like inside and outside the hospital. The hospital tablet terminal 16 is connected to the Internet 21 instead of the closed area independent network 20.

The closed area PC 11, the patient support service server 17, the patient smartphone 15, and the hospital tablet terminal 16 are all configured with information processing devices including a central processing unit (CPU) and a memory, in which the CPU uses the memory to execute software programs, and accordingly, the functions to be described below are implemented. In the present example, the patient support service server 17 is constructed on a cloud system 22, and thus the CPU and memory of the patient support service server 17 are virtual.

First, sharing of information from the closed area PC 11 to the patient support service server 17 will be described.

The closed area PC 11 stores information to be shared in the DB 12, generates concealed data by compressing and concealing the information to be shared using a predetermined concealment method, and generates a QR code (registered trademark) which is a two-dimensional barcode loaded with the concealed data but not loaded with the concealment information indicating a concealment method. The information to be shared is, for example, information related to patient treatment managed within a hospital. The QR code is printed on a QR code printed matter 19 by the printer 13. The concealment method is determined in advance for each hospital.

FIG. 2 is a view showing an example of the QR code printed matter. The QR code printed matter 19 is a piece of paper provided to each patient. On the QR code printed matter 19, the patient name and patient identification information (patient ID) 31, the hospital name and hospital identification information (hospital ID) 92 of the hospital that provides treatment for the patient, a QR code 33 described above, and a patient treatment schedule 34 are printed. The treatment schedule 34 is also loaded on the QR code 33 as information to be shared, but is also printed for the patient's convenience.

The QR code on the QR code printed matter 19 is read and decoded by the camera function of the patient smartphone 15. Concealed data that is the decoding result is sent to the patient support service server 17. The patient support service server 17 stores information on the above-described concealment method in advance, decrypts the concealed data based on the concealment method, and acquires the information to be shared.

Next, sharing of information from the patient support service server 17 to the closed area PC 11 will be described.

The patient support service server 17 stores information to be shared in the DB 18, and generates concealed data by compressing and concealing the information to be shared using a concealment method corresponding to the hospital in which the closed area PC 11 is installed. The information to be shared is, for example, information related to the patient's health that is periodically acquired by the patient smartphone 15. The patient support service server 17 generates a QR code loaded with the concealed data but not loaded with the concealment information indicating the concealment method.

For example, the hospital tablet terminal 16 can acquire QR code data from the patient support service server 17 and display the QR code data on the screen.

FIG. 3 is a view showing an example of the QR code display screen. A QR code display screen 41 displays a hospital name and hospital ID 42, and a plurality of QR codes 43 of designated patients. For example, on the hospital side, one possible usage method is to designate all patients scheduled for treatment on a certain day and acquire the QR codes.

The QR code 43 on the QR code display screen 41 displayed on the hospital tablet terminal 16 is photographed by the camera 14 and imported into the closed area PC 11. The closed area PC 11 stores a concealment method corresponding to its own hospital in advance, decodes the QR code to acquire the concealed data, and decrypts the concealed data based on the concealment method.

Below, the configuration and operation of the system and device will be further described in detail.

FIG. 4 is a block diagram showing a configuration of the collaborative medical system and each device.

The DB 12 stores individual treatment information 58, concealment information 59, and individual health-related information 60. The DB 18 includes a concealment information table 70, individual treatment information 71, treatment hospital information 72, and individual health-related information 73.

The individual treatment information 58 is information related to individual treatment for each patient, which is input by a doctor or the like from the closed area PC 11 at the hospital. The individual treatment information 71 is information that is provided by the individual treatment information 58 from the closed area PC 11 to the patient support service server 17 via the QR code printed matter 19. The individual treatment information 58 and the individual treatment information 71 are basically the same information.

FIG. 5 is a view showing an example of individual treatment information. In the individual treatment information 58 and 71, a disease name 103, treatment schedule information 104, and the like are recorded in association with a patient ID 102 that identifies each patient. By sharing the individual treatment information 71 with the patient support service server 17, it becomes possible to provide a service using the individual treatment information in the patient support service. For example, it becomes possible for a patient to display their own treatment schedule using the patient smartphone 15.

The individual health-related information 73 is information related to individual health management for each patient, which is input by each patient from the patient smartphone 15, collected and accumulated in the patient support service system 17. The individual health-related information 60 is information that is provided by the individual health-related information 73 from the patient support service server 17 to the closed area PC 11 via the display screen of the hospital tablet terminal 16. The individual health-related information 73 and the individual health-related information 60 are basically the same information. FIG. 6 is a view showing an example of individual health-related information. In the individual health-related information 60 and 73, information such as a health status 123, body temperature 124, and blood pressure 125 is recorded in association with a patient ID 121 and an acquired date 122. The health status 123 is information selected by the patient from options such as good, normal, and poor as appropriate for their health status. The individual health-related information 60 and 73 may further include information such as whether the patient has taken medication, eaten a meal, and how much sleep the patient has taken. By sharing the individual health-related information 60 with the closed area PC 11, for example, a doctor can utilize information related to daily health management of a patient for treatment.

The concealment information 59 is information indicating the concealment method corresponding to the own hospital. The concealment information table 70 is information including the concealment information 59 of each hospital. FIG. 7 is a view showing an example of a concealment information table. In the concealment information table 70, concealment information 93 is recorded in association with the hospital ID 92. The concealment information 93 indicates the concealment method used when the information to be shared is concealed, and is information that is also required when decrypting the information to be shared from the concealed data. Concealment in the present example involves archiving the information to be shared with data compression using a compression method determined by each hospital to generate a zip file, and extracting information indicating the compression method from the zip file. Accordingly, the concealed data cannot be easily decrypted. The compression method is a concealment method, and information indicating the compression method is concealment information. Note that in the example of FIG. 7, different compression methods are allocated to each hospital, but the invention is not limited thereto. When the types of compression methods are limited and the number of hospitals is larger than that, the hospitals may be distributed to a plurality of compression methods, for example.

The treatment hospital information 72 is information indicating in which hospital each patient is receiving treatment. FIG. 8 is a view showing an example of treatment hospital information. In the treatment hospital information 72, a hospital ID 112 of the hospital where the patient is receiving treatment is recorded in association with a patient ID 111 of each patient. The treatment hospital information 72 is registered from the patient smartphone 15 of each patient.

Returning to FIG. 4, the closed area PC 11 includes an information concealment unit 51, a code generation unit 52, a printing unit 53, an information decryption unit 54, a code decoding unit 55, an image acquisition unit 6, and an information input unit 57. The patient smartphone 15 includes an image acquisition unit 61, a registration reception unit 62, a physical condition information acquisition unit 63, and a code decoding unit 64. The patient support service server 17 includes a registration processing unit 65, a physical condition information accumulation unit 66, an information decryption unit 67, an information concealment unit 68, and a code generation unit 69. The hospital tablet terminal 16 includes a display unit 32.

The processing flow of the entire collaborative medical system will be described below, including the operations of each unit.

FIG. 9 is a flowchart of individual treatment information sharing processing. The individual treatment information sharing processing is processing of sharing information from the closed area PC 11 to the patient support service server 17. It is assumed that the individual treatment information 58 is registered in the DB 12 in advance by the information input unit 57 operated by a doctor or the like.

First, app usage registration is performed between the patient smartphone 15 used by the patient and the patient support service server 17 (step S101). When a patient installs a patient support service application on the patient smartphone 15 and inputs their full name and attribute information from the registration screen of the application, the input information is registered in the patient support service server 17. The app usage registration allows the patient to use the patient support service provided by the patient support service server 17.

On the other hand, in the closed area PC 11 of the hospital where the patient receives treatment, for example, when the patient receives treatment or medical examination, QR code printed matter output processing is performed (step S102).

FIG. 10 is a flowchart of QR code printed matter output processing.

First, the closed area PC 11 reads the individual treatment information 58 of the target patient from the DB 12 (step S201). In the closed area PC 11, the information concealment unit 51 archives the individual treatment information 58 with compression using the compression method indicated by the concealment information 59 of the own hospital, and generates a zip file (step S202). The information concealment unit 51 performs concealment by extracting the information in the field in which the compression method is described from the zip file, and generates concealed data (step S203). Next, the code generation unit 52 encodes the hospital ID of the own hospital and the concealed data generated in step S203 to generate a hospital identification information & individual treatment information QR code.

FIG. 11 is a view showing an example of hospital identification information & individual treatment information QR code. As shown in FIG. 11, the hospital identification information & individual treatment information QR code 33 is loaded with a hospital ID file 81 and a zip file 82 in which the individual treatment information 58 is compressed and loaded. The zip file 82 has a compression method field in a local header 83 and a central directory entry 84. Concealment is implemented by extracting information of the compression method part. Note that although the present example shows an example in which only the compression method part is extracted, the present invention is not limited thereto. As another example, in addition to the compression method, information in other areas of the central directory entry and local header, such as the created version and the version required for decompression, may also be extracted. Although the zip file 82 in FIG. 11 is loaded with a plurality of files, the number of files is not particularly limited, and may be one, for example.

Returning to FIG. 10, next, the printing unit 53 prints the QR code printed matter 19 including the hospital identification information & individual treatment information QR code 33 (step S205).

Returning to FIG. 9, the QR code printed matter 19 printed in step S102 is given to the patient. The patient can visually check the treatment schedule 34 on the QR code printed matter 19 illustrated in FIG. 2. Accordingly, when the patient registers for the patient support service provided by the patient support service server 17, the information included in the individual treatment information 58 illustrated in FIG. 5 can be confirmed on the patient smartphone 15.

When a patient photographs the hospital identification information & individual treatment information QR code 33 on the QR code printed matter 19 using the patient support service application on the patient smartphone 15, the image acquisition unit 61 on the patient smartphone 15 acquires an image of the hospital identification information & individual treatment information QR code 33, and the code decoding unit 64 decodes the hospital identification information & individual treatment information QR code 33 (step S103).

Subsequently, the patient smartphone 15 displays an application menu (step S104). The menu items include hospital registration and individual treatment information registration. Hospital registration is a procedure for registering the hospital where a patient will receive treatment, and is only required for the first time. Individual treatment information registration s processing for registering the individual treatment information 58 published by a hospital, and should be performed every time a QR code printed matter 19 is received at the hospital.

Here, it is assumed that the patient has selected hospital registration. Thereby, hospital registration processing is performed by the patient smartphone 15 and the patient support service server 17 (step S105).

Note that although here, an example is shown in which the hospital registration processing and the individual treatment information registration processing are selected by the patient from a menu, the invention is not limited thereto. As another example, the selection may be made automatically using the patient smartphone 15. For example, the hospital registration processing may be selected when the QR code is read for the first time for the patient, and the individual treatment information registration processing may be selected from the next time.

FIG. 12 is a flowchart of hospital registration processing.

First, in the patient smartphone 15, the registration reception unit 62 acquires the hospital ID from the decoding result file 81 obtained in step S103 (step S301). The registration reception unit 62 transmits the hospital ID acquired in step S301 to the patient support service server 17 together with the patient ID (step S302). In the patient support service server 17, the registration processing unit 65 records the association between the received patient ID and hospital ID in the DB 18 as treatment hospital information 72. Then, the hospital registration is complete. From the next time, each time the patient receives the QR code printed matter 19 at the hospital, the patient registers individual treatment information.

Returning to FIG. 9, when a patient photographs the hospital identification information & individual treatment information QR code 33 on the QR code printed matter 19 using the patient support service application on the patient smartphone 15, the image acquisition unit 61 on the patient smartphone 15 acquires an image of the hospital identification information & individual treatment information QR code 33, and the code decoding unit 64 decodes the hospital identification information & individual treatment information QR code 33 (step S106).

Subsequently, the patient smartphone 15 displays an application menu (step S107). Here, it is assumed that the patient has selected individual treatment information registration. Thereby, individual treatment information registration processing is performed by the patient smartphone 15 and the patient support service server 17 (step S108).

FIG. 13 is a flowchart of the individual treatment information registration processing.

First, in the patient smartphone 15, the code decoding unit 64 acquires concealed data from the decoding result obtained in step S106 (step S401). The code decoding unit 64 transmits the concealed data acquired in step S401 to the patient support service server 17 together with the patient ID (step S402).

In the patient support service server 17, the information decryption unit 67 specifies the hospital ID corresponding to the received patient ID based on the treatment hospital information 72 (step S403). Subsequently, the information decryption unit 67 specifies the compression method associated with the hospital ID based on the concealment information table 70 (step S404). The information decryption unit 67 complements the concealed data with information on the compression method to acquire a complete zip file (step S405), and decompresses the zip file to acquire individual treatment information 58 (step S406). The information decryption unit 67 registers the acquired individual treatment information 58 in the DB 18 as individual treatment information 71 (step S407). Then, one session of individual treatment information registration is complete. The individual treatment information registration is executed repeatedly.

FIG. 14 is a flowchart of individual physical condition-related information sharing processing. The individual physical condition-related information sharing processing is a processing of sharing information from the patient support service server 17 to the closed area PC 11.

The patient periodically inputs information including information related to their physical condition from the patient smartphone 15, and in the patient smartphone 15, the physical condition information acquisition unit 63 acquires the input information (step S501). The physical condition information acquisition unit 63 then transmits the acquired information together with the patient ID to the patient support service server 17 (step S502). The patient support service server 17 accumulates individual health-related information 73 for each patient based on the received patient ID (step S503). The individual health-related information 73 becomes information to be shared.

Next, processing of sharing the individual health-related information 73 with the closed area PC 11 is performed.

First, QR code display processing is performed by the hospital tablet terminal 16 and the patient support service server 17 (step S504). Thereby, the QR code display screen 41 illustrated in FIG. 3 is displayed on the hospital tablet terminal 16.

FIG. 15 is a flowchart of the QR code display processing.

On the hospital tablet terminal 16, a doctor, a hospital staff, and the like designate a patient for whom individual health-related information is to be acquired (step S601). Information on the designated patient is transmitted to the patient support service server 17.

In the patient support service server 17, the information concealment unit 68 reads the individual health-related information 73 of the designated patient from the DB 18.

Next, the information concealment unit 68 acquires, from the concealment information table 70, a compression method corresponding to the hospital to which the individual health-related information 73 is to be shared, and uses the acquired compression method to compress the individual health-related information 73 of each patient and generate the compressed data (step S603). Next, the information concealment unit 68 generates concealed data by extracting the information on the compression method from the header of the compressed data.

Subsequently, the code generation unit 69 generates an individual health-related information QR code loaded with the concealed data for each patient (step S605). The code generation unit 69 transmits the data of the individual health-related information QR code to the hospital tablet terminal 16 (step S606).

In the hospital tablet terminal 16, the display unit 32 displays the QR code display screen 41 on which the individual health-related information QR code of each patient is arranged (step S607).

Returning to FIG. 14, the closed area PC 11 acquires the individual health-related information 73 of each patient through the individual health-related information import processing (step S505).

FIG. 16 is a flowchart of the individual health-related information import processing.

The QR code display screen 41 displayed on the hospital tablet terminal 16 is photographed by the camera 14 (step S701). In the closed area PC 11, the image acquisition unit 56 imports the image of the individual health-related information QR code, and the code decoding unit 55 acquires the concealed data of each patient by decoding the QR code (step S702).

Subsequently, the information decryption unit 54 acquires information on the compression method corresponding to the own hospital from the concealment information 59, and generates a complete zip file by adding the information to the concealed data (step S703). The information decryption unit 54 decompresses the zip file and acquires the individual health-related information 73 of each patient (step S704).

Returning to FIG. 14, the closed area PC 11 records the individual health-related information 73 in the DB 12 as the individual health-related information 60 in the csv file format (step S506).

As described above, according to the present example, since information to be shared is exchanged using two-dimensional barcodes that do not include information indicating the concealment method, highly confidential information can be exchanged between devices of which networks are separated from each other. In particular, it becomes possible to exchange information between the hospital information system separated from the Internet 21 and the patient smartphone 15 and the patient support service server 17 connected to the Internet 21.

In the present example, since an archive file format is used and information on the compression method is extracted to conceal the information, highly confidential information can be easily exchanged between devices of which networks are separated from each other.

In the present example, since the compression method is associated with each hospital, it is possible to easily implement a patient support service that shares information to be shared with the closed area PCs 11 of a plurality of hospitals.

Example 2

In the first example, an example was shown in which the individual health-related information 73 for each patient is loaded into one QR code and exchanged, but other configurations are also possible. In Example 2, a case is exemplified where a part of the collaborative medical system of Example 1 is modified to exchange the individual health-related information 73 using a plurality of QR codes when the data amount of the individual health-related information 73 is large.

FIG. 17 is a conceptual diagram for describing processing regarding individual health-related information according to Example 2. FIG. 18 is a flowchart of QR code display processing according to Example 2. FIG. 19 is a flowchart of individual health-related information import processing according to Example 2.

In Example 2, the patient support service server 17 and the hospital tablet terminal 16 execute the QR code display processing shown in FIG. 18, and the closed area PC 11 executes the individual health-related information import processing shown in FIG. 19. Example 2 is basically the same as Example 1 with respect to other configurations and processing.

Referring to FIGS. 18 and 17, in Example 2 as well, the patient support service server 17 performs archiving with compression on the individual health-related information 73 of the designated patient from the hospital tablet terminal 16 to generate a zip file, and the processing of concealing a zip file by extracting compression method information from the zip file is the same as in Example 1 (steps S601 to S604).

In Example 2, thereafter, the code generation unit 69 in the patient support service server 17 divides the zip file (concealed data zip') from which the compression method information has been extracted into data blocks of a predetermined size that can be loaded on the QR code (step S801), and generates the individual health-related information QR code for each data block (step S802). Here, a serial number indicating the order of the data blocks is added to each QR code as special header information. For example, a specific code (for example, 0xFFEE) may be used as the signature, and the following 2-byte code may be used as information on the serial number of the data block.

Then, the code generation unit 69 transmits the individual health-related information QR code group to the hospital tablet terminal 16 (step S803). In the hospital tablet terminal 16, the display unit 32 displays the individual health-related information QR code group on the screen (step S804).

Referring to FIGS. 19 and 17, in the closed area PC 11 which is a sharing destination, the QR code display screen displayed on the hospital tablet terminal 16 is photographed by the camera 14 (step S901). In the closed area PC 11, the image acquisition unit 56 recognizes the areas of the plurality of individual health-related information QR codes and imports the images (step S902). Then, the code decoding unit 55 decodes the individual health-related information QR code of each area and acquires the data blocks and serial number information (step S903). The code decoding unit 55 restores the concealed data zip' by combining the data blocks in the order indicated by the serial number information (step S904).

Thereafter, as in Example 1, the information decryption unit 54 acquires information on the compression method corresponding to the own hospital from the concealment information 59, generates a complete zip file by adding the information to the concealed data (step S703), and decompresses the zip file to acquire the individual health-related information 73 (step S704).

As described above, according to the present example, since the concealed data is divided into divided files of a predetermined size or less and exchanged, it is possible to exchange large-sized information to be shared.

Here, an example is described in which one piece of individual health-related information is divided and loaded into a plurality of QR codes and exchanged, but it is also possible to load and exchange a plurality of individual health-related information files by dividing the individual health-related information files into a plurality of QR codes. Then, in step S802, the code generation unit 69 may load the file number and data block serial number information in special header information to be added to each QR code. Then, in the closed area PC 11, in step S903, the code decoding unit 55 acquires the file numbers and serial numbers of a plurality of data blocks, and in step S904, the data blocks with the same file number may be combined in the order of the serial numbers.

Example 3

In Examples 1 and 2, when the patient support service server 17 acquires the individual treatment information 58 from the QR code printed matter 19 printed by the closed area PC 11, the patient support service server 17 registers the individual treatment information 58 as the individual treatment information 71 in the DB 18. In Example 3, a partially modified version of the collaborative medical system of Example 1 will be exemplified. In Example 3, the patient support service server 17 records the individual treatment information 58 acquired from the QR code printed matter 19 as individual treatment information 71 when the individual treatment information 58 is newer than the individual treatment information 71 recorded in the DB 18, and discards the individual treatment information 58 when the individual treatment information 58 is older than the individual treatment information 71. Thereby, it is possible to prevent the updated individual treatment information from being reversed to the old version in the DB 18.

FIG. 20 is a view showing an example of individual treatment information according to Example 3. FIG. 21 is a flowchart of individual treatment information registration processing according to Example 3.

Referring to FIG. 20, the individual treatment information 58 and 71 of Example 3 differs from those of Examples 1 and 2 in that a publication date and time 105 is recorded in association with the patient ID 102 that identifies each patient.

Referring to FIG. 21, the individual treatment information registration processing in Example 3 is similar to that in Example 1 from steps S401 to S406. In Example 3, after step S406, the information decryption unit 67 compares the publication date and time 105 of the individual treatment information 58 acquired in step S406 with the publication date and time 105 of the individual treatment information 71 registered in the DB 18 (step S1001). When the publication date and time 105 of the individual treatment information 58 is older than the publication date and time 105 of the individual treatment information 71, the information decryption unit 67 discards the individual treatment information 58 acquired in step S406 (step S1002). On the other hand, when the publication date and time 105 of the individual treatment information 58 is newer than the publication date and time 105 of the individual treatment information 71, the information decryption unit 67 stores the individual treatment information 58 as new individual treatment information 71 in the DB 18 (step S1003).

As described above, in the present example, the publication date and time of the individual treatment information 71 recorded in the DB 18 is managed, the individual treatment information 58 newly read from the two-dimensional barcode is discarded without being recorded in the DB 18 when the individual treatment information 58 is older than the individual treatment information 71 recorded in the DB 18, and thus, even when the QR code on the old piece of paper is read, the individual treatment information 71 can be prevented from being overwritten with old information.

The above-described embodiments of the present invention are examples for describing the present invention, and are not intended to limit the scope of the present invention only to these embodiments. Those skilled in the art can realize the present invention in various other forms without departing from the scope of the present invention.

REFERENCE SIGNS LIST

11: Closed area PC
12: Database
13: Printer
14: Camera
15: Patient smartphone
16: Hospital tablet terminal
17: Patient support service server
18: Database
19: QR code printed matter
20: Closed area independent network
21: Internet
22: Cloud system
31: Patient ID
32: Display unit
33: Hospital identification information & individual treatment information QR code
34: Treatment schedule
41: QR code display screen
42: Hospital ID
43: QR code
51: Information concealment unit
52: Code generation unit
53: Printing unit
54: Information decryption unit
55: Code decoding unit
56: Image acquisition unit
57: Information input unit
58: Individual treatment information
59: Concealment information
60: Individual health-related information
61: Image acquisition unit
62: Registration reception unit
63: Physical condition information acquisition unit
64: Code decoding unit
65: Registration processing unit
66: Physical condition information accumulation unit
67: Information decryption unit
68: Information concealment unit
69: Code generation unit
70: Concealment information table
71: Individual treatment information
72: Treatment hospital information
73: Individual health-related information
81: File
82: zip file
83: Local header
84: Central directory entry
92: Hospital ID
93: Concealment information
102: Patient ID

103: Disease name
104: Treatment schedule information
105: Publication date and time
111: Patient ID
112: Hospital ID
121: Patient ID
122: Date
123: Health status
124: Body temperature
125: Blood pressure

The invention claimed is:

1. An information transmission system comprising:

an information output device comprising a first computer that stores information to be shared, generates concealed data by compressing and concealing the information to be shared using a predetermined concealment method, and generates a two-dimensional barcode loaded with the concealed data but not loaded with concealment information indicating the concealment method; and an information input system comprising a second computer that stores the concealment method in advance, decodes the two-dimensional barcode to acquire the concealed data, and decrypts the concealed data based on the concealment method, wherein the concealment method is archiving accompanied by data compression using a predetermined compression method, wherein the information output device archives the information to be shared to generate an archive file, generates the concealed data by extracting the information of the compression method included in a header of the archive file, and loads the concealed data to the two-dimensional barcode, wherein the information input system stores information indicating the compression method in advance, the archive file is restored by adding information indicating the compression method to the concealed data, and the information to be shared is extracted from the archive file, wherein the information output device is an information processing device connected only to a closed network of a hospital separated from the Internet, wherein a compression method is predetermined for each hospital, wherein the information output device archives the information to be shared with data compression using the compression method of the hospital, generates the concealed data by extracting the information of the compression method included in the header of the generated archive file, and generates a two-dimensional barcode loaded with the hospital identification information of the hospital and the concealed data, and wherein the information input system stores a correspondence between the hospital identification information and the compression method in advance, decodes the two-dimensional barcode to acquire the hospital identification information and the concealed data, restores the archive file by adding a compression method associated with the hospital identification information to the concealed data, and extracts the information to be shared from the archive file.

2. The information transmission system according to claim 1, wherein the information output device divides the concealed data into a plurality of divided files of a predetermined size or less, and generates the two-dimensional barcode loaded with the divided file and adds a header with a number of the divided file in the concealed data for each piece of the divided files, and the information input system decodes the plurality of two-dimensional barcodes to acquire the divided files, acquires the number from the header, and combines the plurality of divided files based on the number to generate the concealed data.

3. The information transmission system according to claim 1, wherein the information to be shared includes or is added with information on the publication date and time, and the information input system records the information to be shared obtained from the concealed data in a database together with the publication date and time, records the newly obtained information to be shared in the database when the publication date and time of the newly obtained information to be shared is newer than the publication date and time of the information to be shared recorded in the database, and discards the newly obtained information to be shared without recording the newly obtained information to be shared in the database when the publication date and time of the newly obtained information to be shared is older than the publication date and time of the information to be shared recorded in the database.

4. The information transmission system according to claim 1, wherein the information output device prints the two-dimensional barcode on a piece of paper or displays the two-dimensional barcode on a screen, and the information input system photographs the two-dimensional barcode on the piece of paper or the screen.

5. The information transmission system according to claim 1, wherein the information input system includes a terminal device carried by each patient and a server device connectable to the terminal device via the Internet.

6. An information output device for transmitting information to be shared to an information input system comprising:

a database that stores information to be shared;

a first computer configured to:

generate concealed data by compressing and concealing the information to be shared using a predetermined concealment method, and generate a two-dimensional barcode loaded with the concealed data but not loaded with the concealment information indicating the concealment method, wherein the concealment method is archiving accompanied by data compression using a predetermined compression method, wherein the information output device archives the information to be shared to generate an archive file, generates the concealed data by extracting the information of the compression method included in a header of the archive file, and loads the concealed data to the two-dimensional barcode, wherein the information input system stores information indicating the compression method in advance, the archive file is restored by adding information indicating the compression method to the concealed data, and the information to be shared is extracted from the archive file, wherein the information output device is an information processing device connected only to a closed network of a hospital separated from the Internet, wherein a compression method is predetermined for each hospital, wherein the information output device archives the information to be shared with data compression using the compression method of the hospital, generates the concealed data by extracting the information of the compression method included in the header of the generated archive file, and generates a two-dimensional barcode loaded with the hospital identification information of the hospital and the concealed data, and wherein the information input system stores a correspondence between the hospital identification information and the compression method in advance, decodes the two-dimensional barcode to acquire the hospital identification information and the concealed data, restores the archive file by adding a compression method associated with the hospital identification information to the concealed data, and extracts the information to be shared from the archive file.

7. An information transmission method for transmitting information to be shared from an information output device to an information input system, the method comprising:

by the information output device:

storing stores information to be shared;

generating concealed data by compressing and concealing the information to be shared using a predetermined concealment method; and generating a two-dimensional barcode loaded with the concealed data but not loaded with concealment information indicating the concealment method; and by an information input system:

storing the concealment method in advance;

decoding the two-dimensional barcode to acquire the concealed data; and decrypting the concealed data based on the concealment method, wherein the concealment method is archiving accompanied by data compression using a predetermined compression method, wherein the information output device archives the information to be shared to generate an archive file, generates the concealed data by extracting the information of the compression method included in a header of the archive file, and loads the concealed data to the two-dimensional barcode, wherein the information input system stores information indicating the compression method in advance, the archive file is restored by adding information indicating the compression method to the concealed data, and the information to be shared is extracted from the archive file, wherein the information output device is an information processing device connected only to a closed network of a hospital separated from the Internet, wherein a compression method is predetermined for each hospital, wherein the information output device archives the information to be shared with data compression using the compression method of the hospital, generates the concealed data by extracting the information of the compression method included in the header of the generated archive file, and generates a two-dimensional barcode loaded with the hospital identification information of the hospital and the concealed data, and wherein the information input system stores a correspondence between the hospital identification information and the compression method in advance, decodes the two-dimensional barcode to acquire the hospital identification information and the concealed data, restores the archive file by adding a compression method associated with the hospital identification information to the concealed data, and extracts the information to be shared from the archive file.

* * * * *